US012515065B1

(12) United States Patent
Zhou

(10) Patent No.: US 12,515,065 B1
(45) Date of Patent: Jan. 6, 2026

(54) BRA HAVING PHYSIOTHERAPY EFFECT

(71) Applicant: Xiaoju Zhou, Ji'an (CN)

(72) Inventor: Xiaoju Zhou, Ji'an (CN)

( * ) Notice: Subject to any disclaimer, the term of this patent is extended or adjusted under 35 U.S.C. 154(b) by 0 days.

(21) Appl. No.: 19/211,260

(22) Filed: May 18, 2025

(51) Int. Cl.
*A61N 5/06* (2006.01)

(52) U.S. Cl.
CPC .... *A61N 5/0613* (2013.01); *A61N 2005/0632* (2013.01); *A61N 2005/0645* (2013.01); *A61N 2005/0659* (2013.01)

(58) Field of Classification Search
CPC .......... A61N 5/0613; A61N 2005/0632; A61N 2005/0645; A61N 2005/0659; A61N 5/06–2005/073
See application file for complete search history.

(56) References Cited

U.S. PATENT DOCUMENTS 11,304,456 B2 * 4/2022 Connor .................. D02G 3/448
2009/0018622 A1 * 1/2009 Asvadi ................. A61N 5/0621
607/91
2019/0159528 A1 * 5/2019 Palmer ..................... A61N 5/06
2021/0325032 A1 * 10/2021 Nanev ....................... F21V 3/04
2021/0337885 A1 * 11/2021 Connor ................ A41C 3/0064

FOREIGN PATENT DOCUMENTS

CN 108991611 A * 12/2018 ........... A61N 5/0624
CN 109419053 A * 3/2019 ........... A61N 5/0625

* cited by examiner

*Primary Examiner* — Jonathan T Kuo
(74) *Attorney, Agent, or Firm* — JEEN IP LAW, LLC

(57) ABSTRACT

The present disclosure is a bra having a physiotherapy effect. The bar includes a flexible outer cover, a transparent flexible lining and several physiotherapy lamp beads arranged between the flexible outer cover and the transparent flexible lining, where the flexible outer cover and the transparent flexible lining each are provided with wrapping cavities for wrapping female breasts, several physiotherapy lamp beads are arranged in the two wrapping cavities of the flexible outer cover, and light emitting surfaces of the physiotherapy lamp beads face the transparent flexible lining to make infrared light emitted by the physiotherapy lamp beads penetrate the transparent flexible lining and irradiate the female breasts.

9 Claims, 5 Drawing Sheets

BRA HAVING PHYSIOTHERAPY EFFECT

TECHNICAL FIELD

The present disclosure relates to the field of physiotherapy clothing, and in particular to a bra having a physiotherapy effect.

BACKGROUND

Under the background of increasing attention to women's health in contemporary society, health management of women's breasts has also received more and more attention. As a safe, non-invasive and effective physical therapy, infrared physiotherapy has shown significant advantages in promoting breast blood circulation and improving breast tissue metabolism, and has been gradually applied to the field of female breast health care.

However, structures having a physiotherapy effect are not designed for existing female bras, and therefore, further improvement needs to be made.

SUMMARY

An objective of the present disclosure is to provide a bra having a physiotherapy effect, which aims at solving the problems that red light emitted by an existing red light physiotherapy bra needs to pass through irradiation holes to irradiate female breasts, which not only affects a utilization rate of the red light, but also causes an overall structure to be complex.

The present disclosure is implemented as follows: a bra having a physiotherapy effect, including a flexible outer cover, a transparent flexible lining and several physiotherapy lamp beads arranged between the flexible outer cover and the transparent flexible lining, where the flexible outer cover and the transparent flexible lining each are provided with wrapping cavities for wrapping female breasts, several physiotherapy lamp beads are arranged in the two wrapping cavities of the flexible outer cover, and light emitting surfaces of the physiotherapy lamp beads face the transparent flexible lining to make infrared light emitted by the physiotherapy lamp beads penetrate the transparent flexible lining and irradiate the female breasts.

Further, the flexible outer cover is made of spandex and cotton blended fabric, and the transparent flexible lining is made of a transparent porous silica gel material.

Further, a physiotherapy cover is arranged between the flexible outer cover and the transparent flexible lining, the physiotherapy cover is also provided with wrapping cavities for wrapping the female breasts, and the physiotherapy lamp beads are arranged on inner walls of the wrapping cavities of the physiotherapy cover.

Further, inner walls of the two wrapping cavities of the physiotherapy cover each are provided with a first spiral groove, a flexible circuit board is arranged in the first spiral groove, and a plurality of physiotherapy lamp beads are sequentially arranged on the flexible circuit board in an extending direction of the flexible circuit board.

Further, a sealed accommodating cavity is arranged at a cover body, located between the two wrapping cavities, of the physiotherapy cover, a printed circuit board (PCB) is arranged in the accommodating cavity, and the two flexible circuit boards are electrically connected to the PCB.

Further, the inner walls of the two wrapping cavities of the physiotherapy cover each are further provided with a second spiral groove, the second spiral groove is located in spiral gaps of the first spiral groove, and a certain distance is set between the first spiral groove and the second spiral groove. A heating element and a temperature sensor are arranged in each second spiral groove, and the heating elements and the temperature sensors are also electrically connected to the PCB.

Further, carbon fiber heating wires or graphene heating films are used as the heating elements, and the PCB is provided with a microprocessor.

Further, the PCB is further provided with a Bluetooth module, the Bluetooth module is electrically connected to the microprocessor, and the microprocessor is in communication connection to a mobile phone APP through the Bluetooth module.

Further, a storage battery is further arranged in the accommodating cavity of the physiotherapy cover, the storage battery is electrically connected to the PCB, a magnetic charging contact is arranged on the PCB, and a contact portion of the magnetic charging contact is exposed out of the accommodating cavity.

Further, the physiotherapy cover is made of a transparent silica gel material, and a ventilation structure is arranged at a position, other than the first spiral groove and the second spiral groove, of a cavity wall of each wrapping cavity of the physiotherapy cover.

Compared with the prior art, the present disclosure has the beneficial effects as follows:

1. According to the present disclosure, by arranging the transparent flexible lining, the red light or infrared light emitted by the physiotherapy lamp beads is enabled to efficiently penetrate the transparent flexible lining to irradiate the female breasts, thereby realizing physiotherapy functions, which not only enables the red light or infrared light to be efficiently utilized, but also makes the structure of the present disclosure be simple and convenient to produce and manufacture.
2. The present disclosure is further provided with the heating elements as heating bodies, the physiotherapy lamp beads and the heating bodies cooperate with each other, physiotherapy light goes deep into breast tissue to play a role, the heating bodies provide an appropriate temperature to promote absorption and blood circulation, the physiotherapy lamp beads and the heating bodies work together to enhance the effect, and layout is reasonable, such that uniformity of the physiotherapy effect on each portion of the breasts is ensured, and health of the breasts is comprehensively protected.
3. The PCB of the present disclosure is further provided with the Bluetooth module, and the microprocessor is in communication connection to the mobile phone APP through the Bluetooth module, such that start and stop of physiotherapy, setting and checking of a heating temperature, etc. can be carried out through the mobile phone APP, which makes use of the present disclosure is more convenient.
4. The present disclosure is provided with the storage battery, such that a user can start an infrared light or heating mode at any time, which effectively improves a use scene of the present disclosure.

In the figures: 1. flexible outer cover; 2. transparent flexible lining; 3. physiotherapy cover; 4. physiotherapy lamp bead; 5. flexible circuit board; 6. printed circuit board (PCB); 7. heating element; 8. storage battery; 9. first spiral groove; 10. second spiral groove; 11. temperature sensor; 12. magnetic charging contact; and 13. wrapping cavity.

DETAILED DESCRIPTIONS OF THE EMBODIMENTS

In the present disclosure, unless otherwise explicitly specified and defined, the terms “mounting”, “connecting”, “connection”, “fixing”, etc. should be understood in a broad sense, for example, they may denote fixed connection, detachable connection, or integrated connection, denote mechanical connection or electrical connection, denote direct connection or indirect connection via an intermediate medium, or denote communication between interiors of two elements or interaction between two elements. The specific meanings of the above terms in the present disclosure may be understood on a case-by-case basis for those of ordinary skill in the art.

A further specification is made below with reference to the accompanying drawings and in conjunction with particular examples:

Example 1

Figure 1:
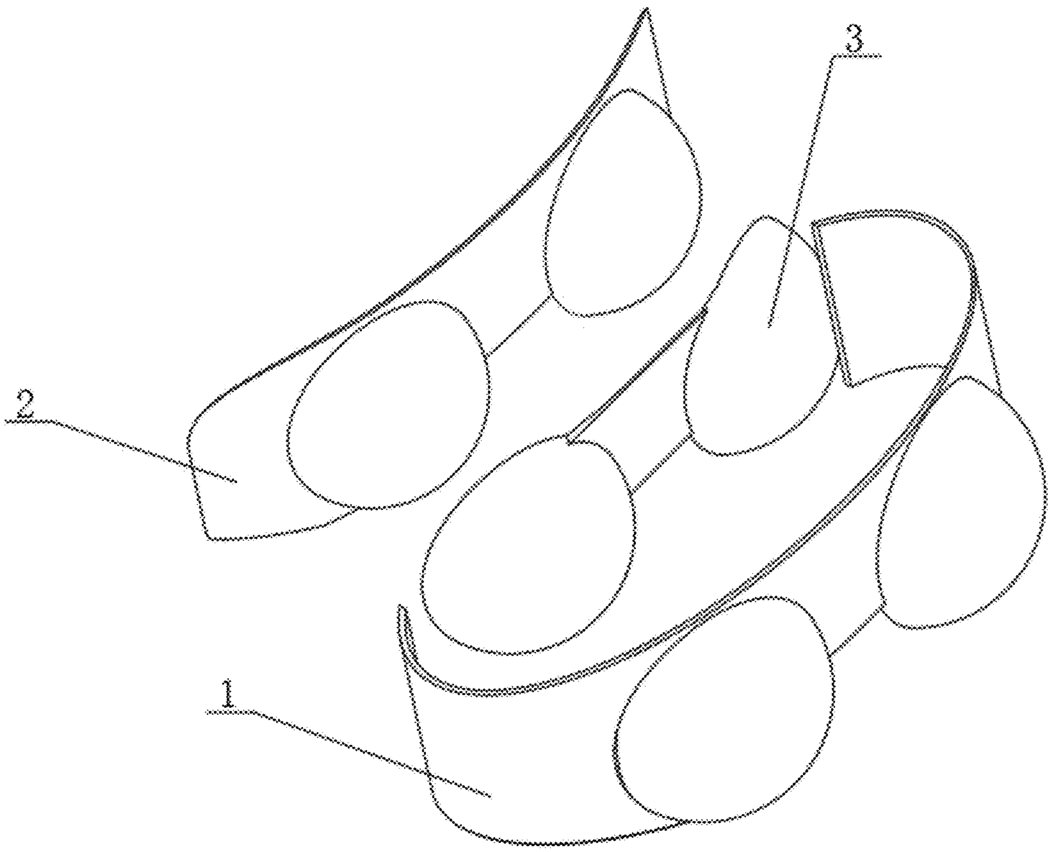
FIG. 1 is an exploded diagram of the present disclosure.

As shown in FIG. 1, a bra having a physiotherapy effect, including a flexible outer cover 1, a transparent flexible lining 2 and a physiotherapy cover 3 arranged between the flexible outer cover 1 and the transparent flexible lining 2. The flexible outer cover 1, the transparent flexible lining 2 and the physiotherapy cover 3 each are provided with wrapping cavities for wrapping female breasts. The flexible outer cover 1 is made of spandex and cotton blended fabric, where the spandex content is about 10%-15%, and the cotton content is about 85%-90%. The blended fabric in this structure has good moisture absorption and air permeability, and has excellent elasticity and flexibility. The transparent flexible lining 2 is made of a medical-grade transparent porous silica gel material, and medical-grade transparent porous silica gel has good biocompatibility, has no irritation to skin, and is safe and reliable. The material has good light transmittance, and can make infrared light efficiently transmitted to a body of a user, thereby ensuring the physiotherapy effect. Moreover, the silica gel material is soft and elastic, fits curves of the breasts of the user, is comfortable to wear, and has certain waterproof property, easy to clean and maintain.

Figure 2:
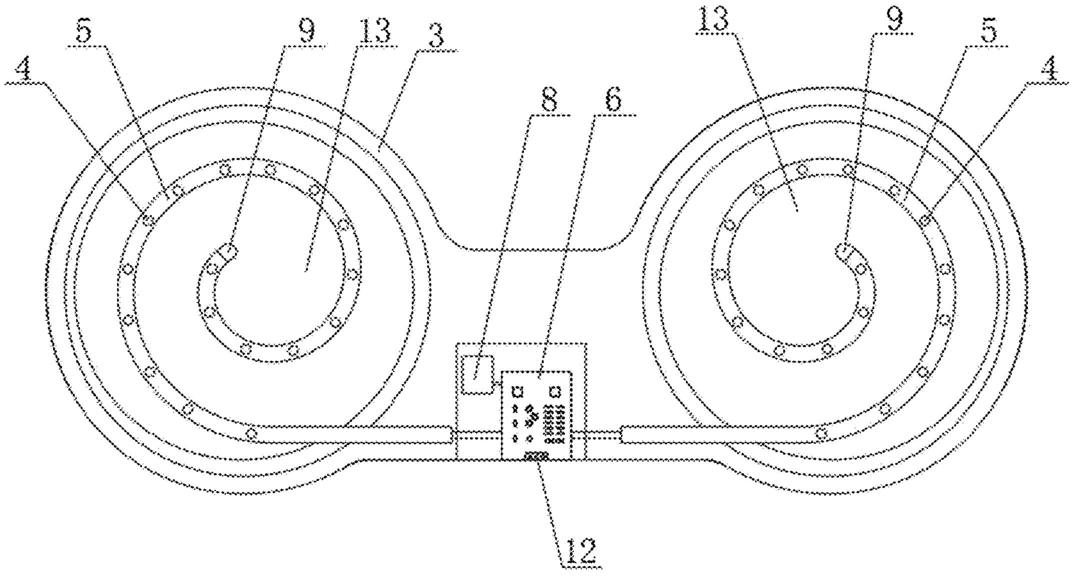
FIG. 2 is a front view of a physiotherapy cover in Example 1 of the present disclosure.
Figure 3:
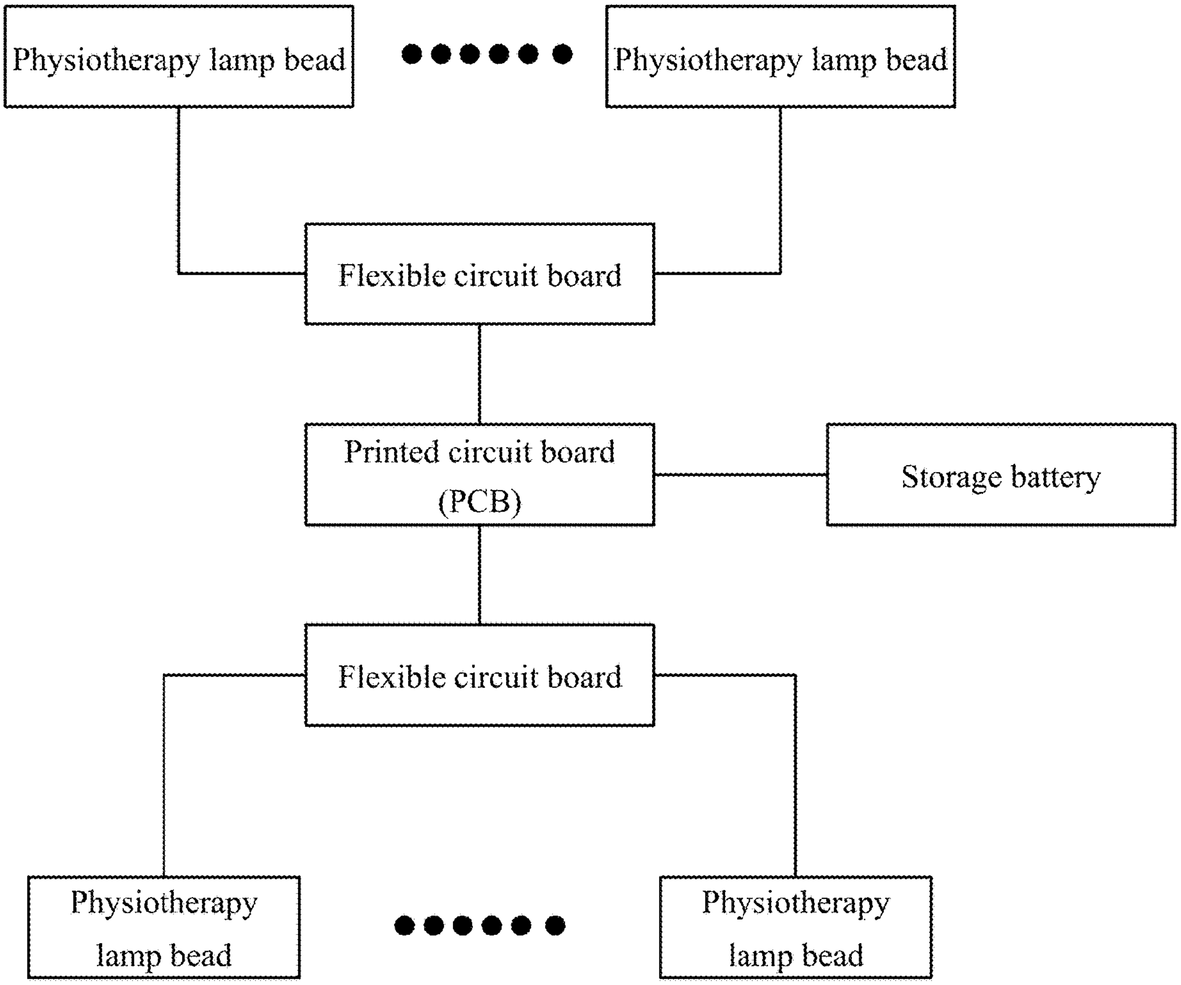
FIG. 3 is a block diagram of an electric control structure in Example 1 of the present disclosure.

As shown in FIGS. 2 and 3, inner walls of the two wrapping cavities of the physiotherapy cover 3 each are provided with a first spiral groove, a flexible circuit board 5 is arranged in the first spiral groove, and a plurality of physiotherapy lamp beads 4 are sequentially arranged on the flexible circuit board 5 in an extending direction of the flexible circuit board. Light emitting surfaces of the physiotherapy lamp beads 4 face the transparent flexible lining 2, and the flexible circuit board 5 and the physiotherapy lamp beads 4 are coated with waterproof nano-coatings. The physiotherapy cover 3 is made of a transparent silica gel material, and a ventilation hole structure is arranged at a position, other than the first spiral groove, of a cavity wall of each wrapping cavity 13 of the physiotherapy cover. The physiotherapy lamp beads 4 are light emitting diode (LED) red lamp beads or LED infrared lamp beads, the red lamp beads can emit red light with a wavelength of 610-670 nm, and the infrared lamp beads can emit infrared light with a wavelength of 810-930 nm. A sealed accommodating cavity is arranged at a cover body, located between the two wrapping cavities, of the physiotherapy cover 3, a printed circuit board (PCB) 6 and a storage battery 8 are arranged in the accommodating cavity, and the storage battery 8 and the two flexible circuit boards 5 are electrically connected to the PCB 6. The storage battery 8 is used for supplying power to the flexible circuit boards 5, the PCB 6 and the physiotherapy lamp beads 4, and red light or infrared light emitted by the physiotherapy lamp beads 4 is irradiated to the female breasts through the transparent flexible lining 2, thereby realizing physiotherapy functions. The PCB 6 is provided with a magnetic charging contact 12, a contact portion of the magnetic charging contact 12 is exposed out of the accommodating cavity, and is used for connecting a charger to charge the storage battery 8, and the magnetic charging contact 12 has a good waterproof effect.

Example 2

Figure 4:
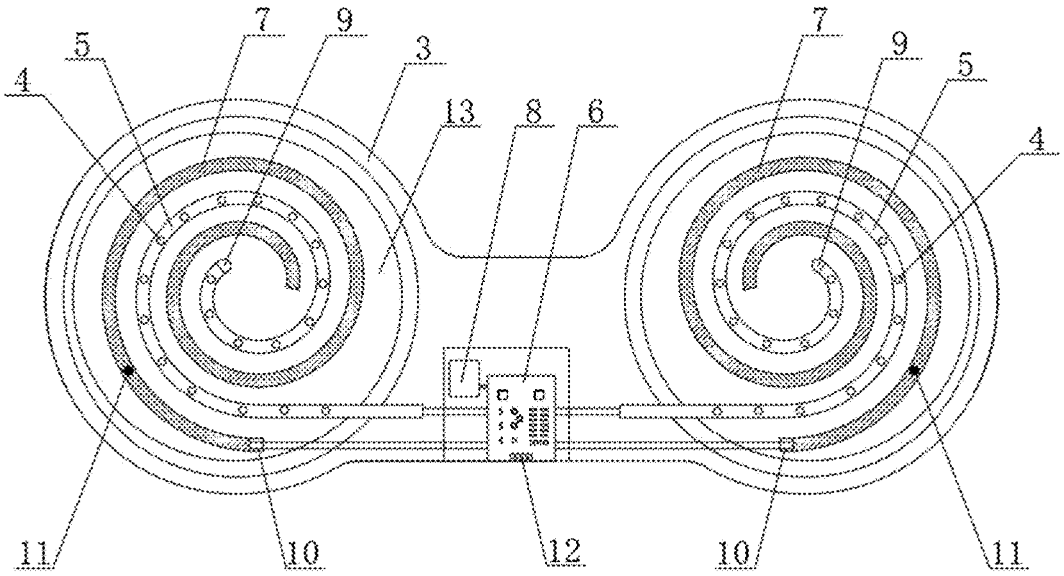
FIG. 4 is a front view of a physiotherapy cover in Example 2 of the present disclosure.
Figure 5:
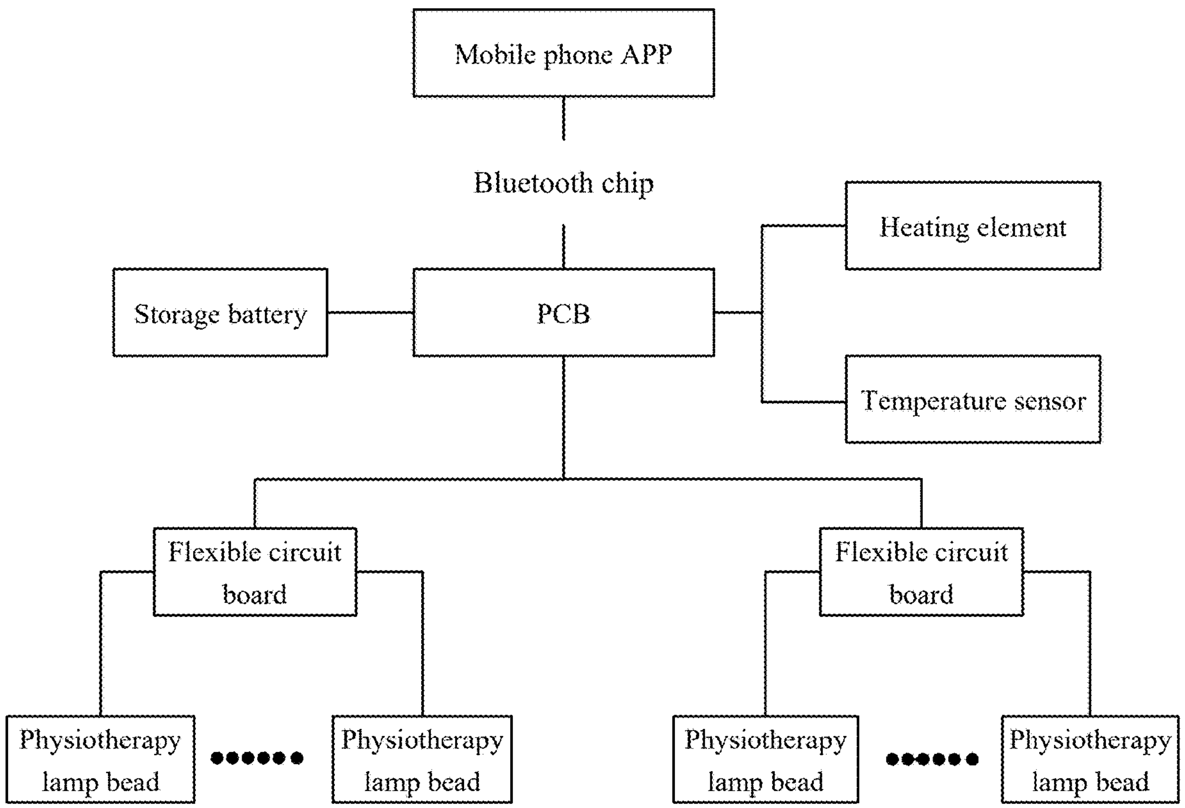
FIG. 5 is a block diagram of an electric control structure in Example 2 of the present disclosure.

Difference between this example and Example 1 lies in that, as shown in FIGS. 4 and 5, in addition to the first spiral groove, the inner walls of the two wrapping cavities of the physiotherapy cover 3 each are provided with a second spiral groove, and the second spiral groove is located in spiral gaps of the first spiral groove. A certain distance is set between the first spiral groove and the second spiral groove, and a ventilation hole structure is arranged at a position, other than the first spiral groove 9 and the second spiral groove 10, of a cavity wall of each wrapping cavity 13 of the physiotherapy cover 3, thereby facilitating heat dissipation and ventilation. A heating element 7 and a temperature sensor 11 are arranged in each second spiral groove, and a surface of each heating element 7 should be coated with an insulating coating and a waterproof nano-coating. The heating elements 7 and the temperature sensors 11 are also electrically connected to the PCB 6. Carbon fiber heating wires or graphene heating films may be used as the heating elements 7, and the PCB 6 is provided with a microprocessor. A temperature threshold of 38° C.-45° C. preset in the microprocessor can effectively control a heating temperature under the joint action of the microprocessor and the temperature sensors 11. By means of the arrangement, the physiotherapy lamp beads 4 and heating bodies cooperate with each other, physiotherapy light goes deep into breast tissue to play a role, the heating bodies provide an appropriate temperature to promote absorption and blood circulation, the physiotherapy lamp beads and the heating bodies work together to enhance the effect, and layout is reasonable, such that uniformity of the physiotherapy effect on each portion of the breasts is ensured, and health of the breasts is comprehensively protected.

In addition, the PCB 6 is further provided with a Bluetooth module, the Bluetooth module is electrically connected to the microprocessor, and the microprocessor is in communication connection to a mobile phone APP through the Bluetooth module, such that start and stop of physiotherapy, setting and checking of a heating temperature, etc. can be carried out through the mobile phone APP, which makes use of the present disclosure is more convenient.

To sum up, in the present disclosure, by arranging the transparent flexible lining 2, the red light or infrared light emitted by the physiotherapy lamp beads 4 is enabled to efficiently penetrate the transparent flexible lining 2 to irradiate the female breasts, thereby realizing physiotherapy functions, which not only enables the red light or infrared light to be efficiently utilized, but also makes the structure of the present disclosure be simple and convenient to produce and manufacture.

The foregoing are merely the preferred embodiments of the present disclosure and are not intended to limit the present disclosure, and various modifications and changes may be made by those skilled in the art. Any modifications, equivalent substitutions, improvements, etc. within the spirit and principles of the present disclosure are intended to fall within the scope of protection of the present disclosure.

What is claimed is:

1. A bra having a physiotherapy effect, comprising a flexible outer cover, a transparent flexible lining and several physiotherapy lamp beads arranged between the flexible outer cover and the transparent flexible lining, wherein the flexible outer cover and the transparent flexible lining each are provided with wrapping cavities for wrapping female breasts, several physiotherapy lamp beads are arranged in the wrapping cavities of the flexible outer cover, and light emitting surfaces of the physiotherapy lamp beads face the transparent flexible lining to make infrared light emitted by the physiotherapy lamp beads penetrate the transparent flexible lining and irradiate the female breasts;

wherein a physiotherapy cover is arranged between the flexible outer cover and the transparent flexible lining;

inner walls of the wrapping cavities of the physiotherapy cover are provided with first spiral grooves, wherein an accommodating cavity is arranged at a cover body, located between the wrapping cavities, of the physiotherapy cover, and a printed circuit board (PCB) is arranged in the accommodating cavity;

wherein the inner walls of the wrapping cavities of the physiotherapy cover are further provided with second spiral grooves, the second spiral grooves are provided in spiral gaps of the first spiral grooves, and there are distances between the first spiral grooves and the second spiral grooves;

heating elements and temperature sensors are arranged in the second spiral grooves, and the heating elements and the temperature sensors are further electrically connected to the PCB.

2. The bra having a physiotherapy effect according to claim 1, wherein the flexible outer cover is made of spandex and cotton blended fabric, and the transparent flexible lining is made of a transparent porous silica gel material.

3. The bra having a physiotherapy effect according to claim 1, wherein the physiotherapy cover is also provided with wrapping cavities for wrapping the female breasts, and the physiotherapy lamp beads are arranged on the inner walls of the wrapping cavities of the physiotherapy cover.

4. The bra having a physiotherapy effect according to claim 3, wherein flexible circuit boards are arranged in the first spiral grooves, and a plurality of physiotherapy lamp beads are sequentially arranged on the flexible circuit boards in an extending direction of the flexible circuit boards.

5. The bra having a physiotherapy effect according to claim 4, wherein the flexible circuit boards are electrically connected to the PCB.

6. The bra having a physiotherapy effect according to claim 1, wherein carbon fiber heating wires or graphene heating films are used as the heating elements, and the PCB is provided with a microprocessor.

7. The bra having a physiotherapy effect according to claim 6, wherein the PCB is further provided with a Bluetooth module, the Bluetooth module is electrically connected to the microprocessor, and the microprocessor is in communication connection to a mobile phone APP through the Bluetooth module.

8. The bra having a physiotherapy effect according to claim 7, wherein a storage battery is further arranged in the accommodating cavity of the physiotherapy cover, the storage battery is electrically connected to the PCB, a magnetic charging contact is arranged on the PCB, and a contact portion of the magnetic charging contact is exposed out of the accommodating cavity.

9. The bra having a physiotherapy effect according to claim 8, wherein the physiotherapy cover is made of a transparent silica gel material, and a ventilation structure is arranged at a position, other than the first spiral grooves and the second spiral grooves, of a cavity wall of each of the wrapping cavities of the physiotherapy cover.

* * * * *